(12) United States Patent
Söderberg

(10) Patent No.: US 8,235,051 B2
(45) Date of Patent: Aug. 7, 2012

(54) NOSE-DILATING DEVICE

(75) Inventor: Leif Söderberg, Lund (SE)

(73) Assignee: Adactive Marketing AB, Lund (SE)

( * ) Notice: Subject to any disclaimer, the term of this patent is extended or adjusted under 35 U.S.C. 154(b) by 316 days.

(21) Appl. No.: 12/521,656

(22) PCT Filed: Dec. 21, 2007

(86) PCT No.: PCT/EP2007/011321
§ 371 (c)(1),
(2), (4) Date: Sep. 8, 2009

(87) PCT Pub. No.: WO2008/077604
PCT Pub. Date: Jul. 3, 2008

(65) Prior Publication Data
US 2010/0031965 A1 Feb. 11, 2010

(30) Foreign Application Priority Data
Dec. 27, 2006 (SE) ........................................ 0602802

(51) Int. Cl.
*A61F 5/56* (2006.01)
*A61M 29/00* (2006.01)
(52) U.S. Cl. ........................................ 128/848; 606/199
(58) Field of Classification Search .............. 606/1, 191, 606/199, 200, 201, 204.45; 128/200.24, 128/203.12, 203.15, 207.18, 206.11, 204.12, 128/206.18, 206.27, 207.13, 848; 604/93.01, 604/94.01, 48
See application file for complete search history.

(56) References Cited

U.S. PATENT DOCUMENTS

| | | | |
|---|---|---|---|
| 3,722,509 A * | 3/1973 | Nebel | 128/204.12 |
| 5,775,335 A | 7/1998 | Seal | |
| 5,895,409 A * | 4/1999 | Mehdizadeh | 606/199 |
| 5,922,006 A | 7/1999 | Sugerman | |

(Continued)

FOREIGN PATENT DOCUMENTS

EP 1676550 A 7/2006

(Continued)

OTHER PUBLICATIONS

International Search Report dated Jun. 23, 2008 in corresponding international patent application No. PCT/EP2007/011321, 4 pages.

*Primary Examiner* — Patricia Bianco
*Assistant Examiner* — Tarla Patel
(74) *Attorney, Agent, or Firm* — Maier & Maier, PLLC

(57) ABSTRACT

The present invention relates to an internal nose-dilating device, comprising two conical inserts, which each have four walls and two openings: a small opening, which during use is oriented inwards towards the nasal cavity, and a large opening, which is oriented out from the nose, the inserts being connected by means of a connecting member, which during use is the only part that remains on the outside of the nose. The four walls of the inserts are convex at their central portions and provided with a substantially horizontal recess, the recess being arranged along the four walls of the inserts and extending at least partly along the circumference on the outside thereof to form a bulge in the four walls of the inserts. The inserts have at least four apertures and a reinforced portion, which is provided along a rounded edge of the small opening, thereby allowing the inserts to be turned inside out.

20 Claims, 6 Drawing Sheets

U.S. PATENT DOCUMENTS

| | | | |
|---|---|---|---|
| 6,004,342 A | 12/1999 | Filis | |
| 6,270,512 B1 | 8/2001 | Rittmann | |
| 6,863,066 B2 | 3/2005 | Ogie | |
| 7,461,651 B2 * | 12/2008 | Brown | 128/200.24 |
| 2002/0177871 A1 | 11/2002 | Santin | |
| 2003/0150449 A1 | 8/2003 | Spinelli | |
| 2003/0181941 A1 | 9/2003 | Bruggisser et al. | |
| 2004/0147954 A1 | 7/2004 | Wood | |
| 2005/0066972 A1 * | 3/2005 | Michaels | 128/206.11 |

FOREIGN PATENT DOCUMENTS

| | | |
|---|---|---|
| WO | 8803788 | 6/1988 |
| WO | 2004/069110 A1 | 8/2004 |
| WO | 2006/010848 | 2/2006 |

\* cited by examiner

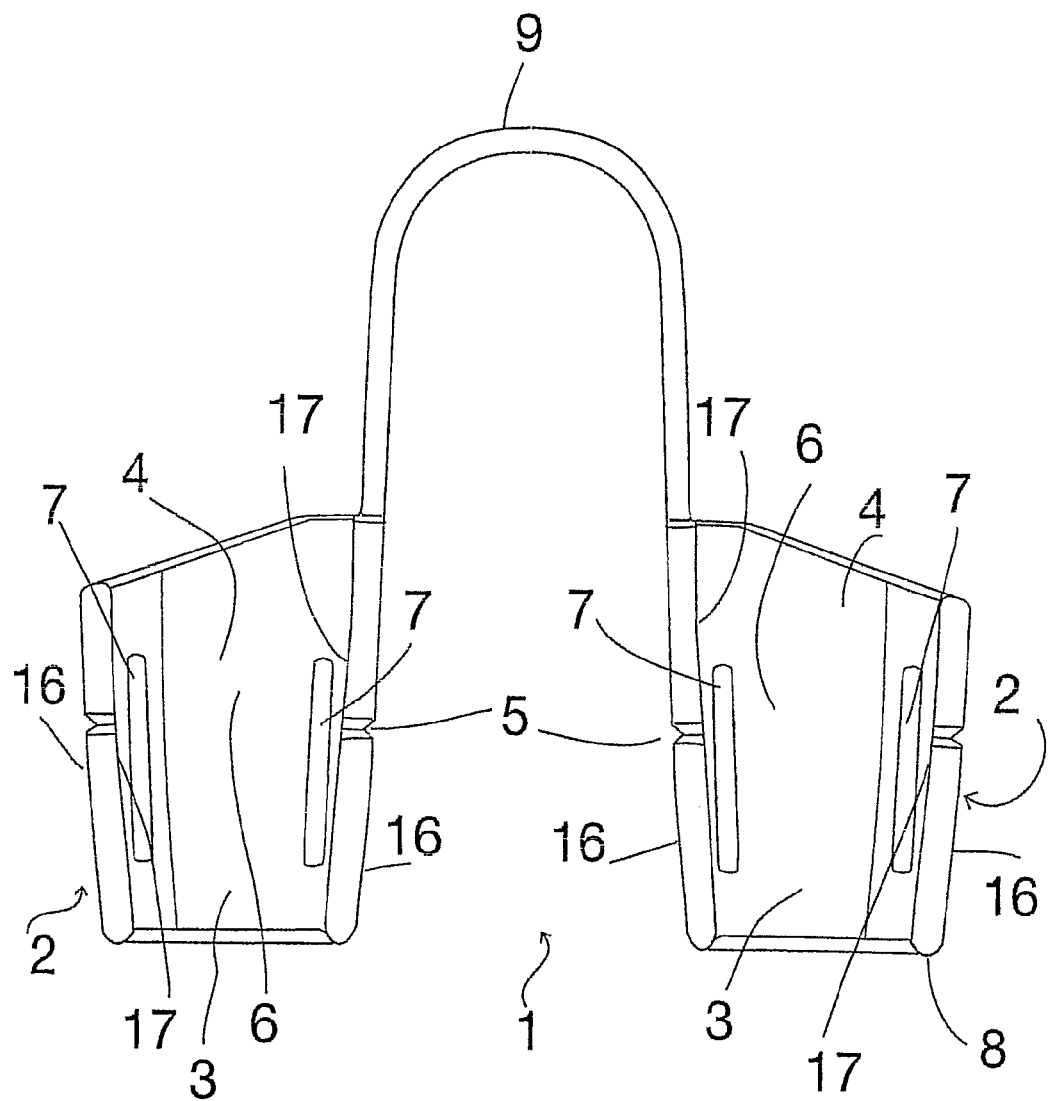
Figur 1

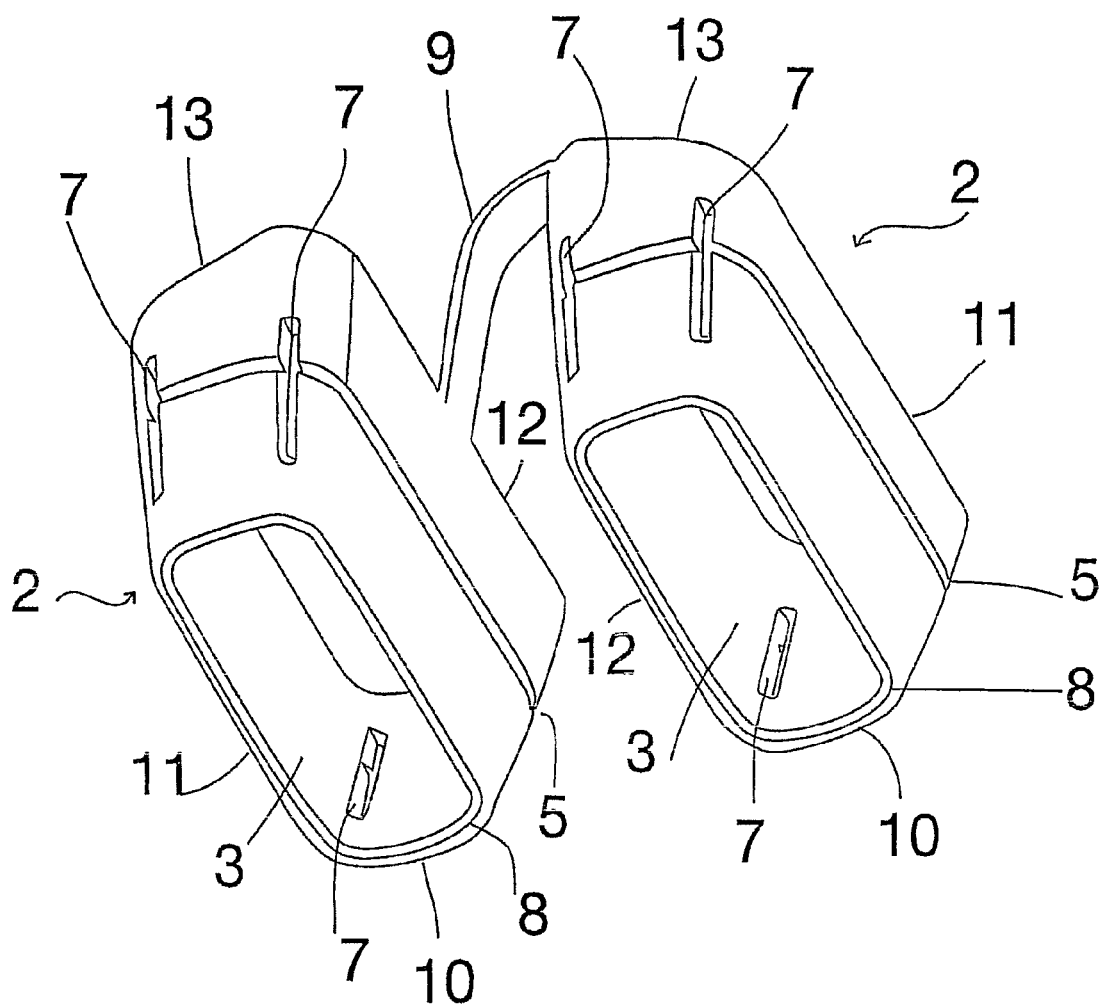
Figur 2

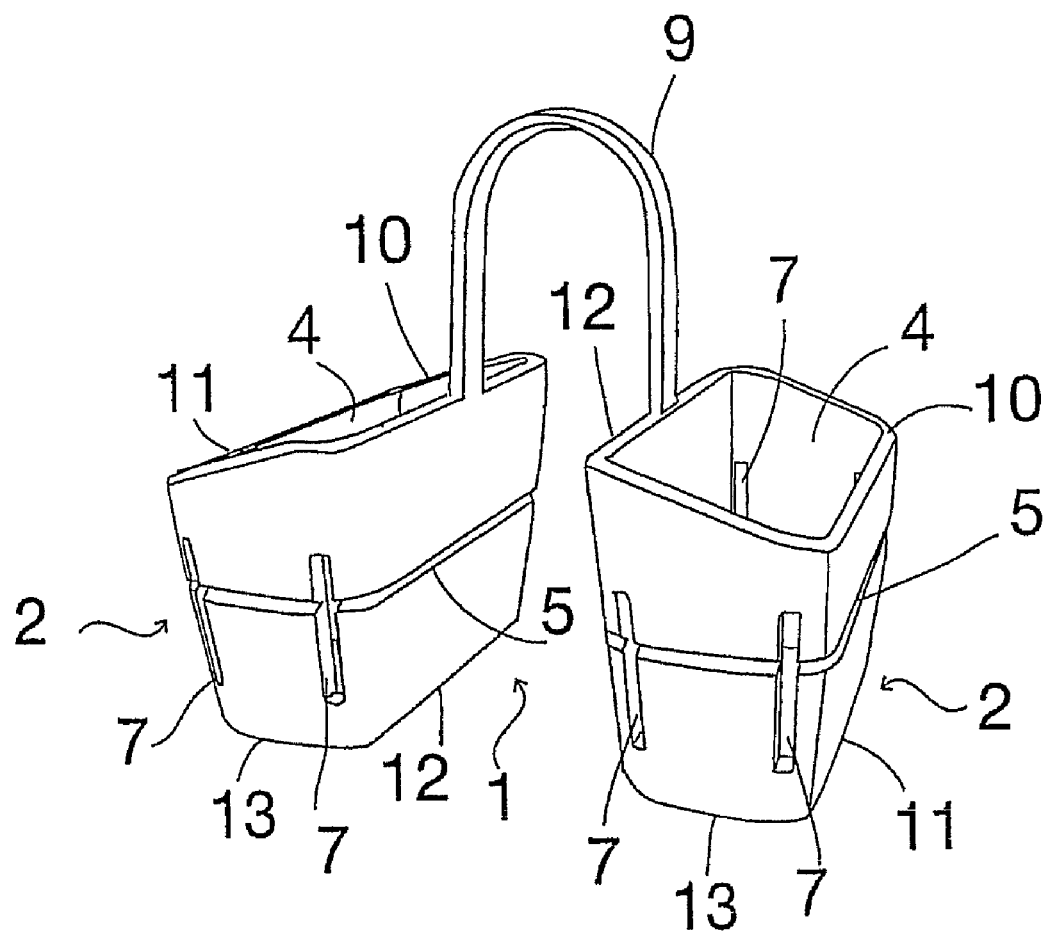
Figur 3

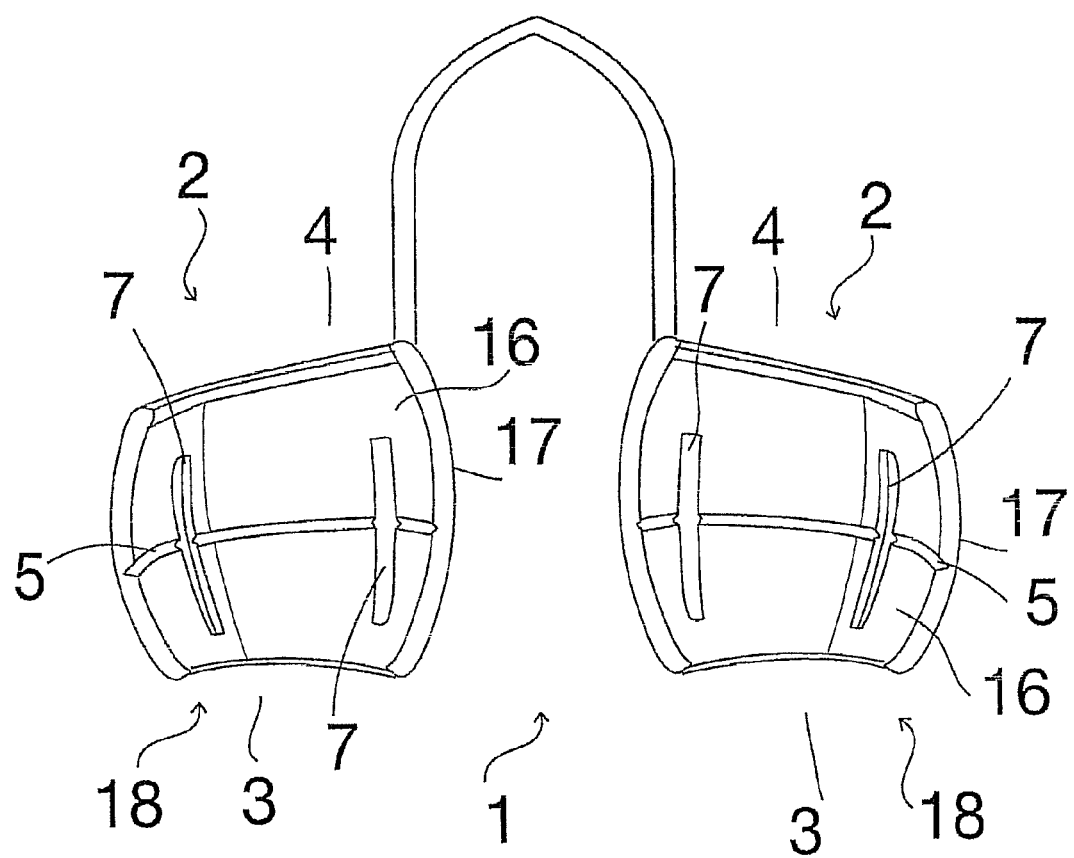
Figur 4

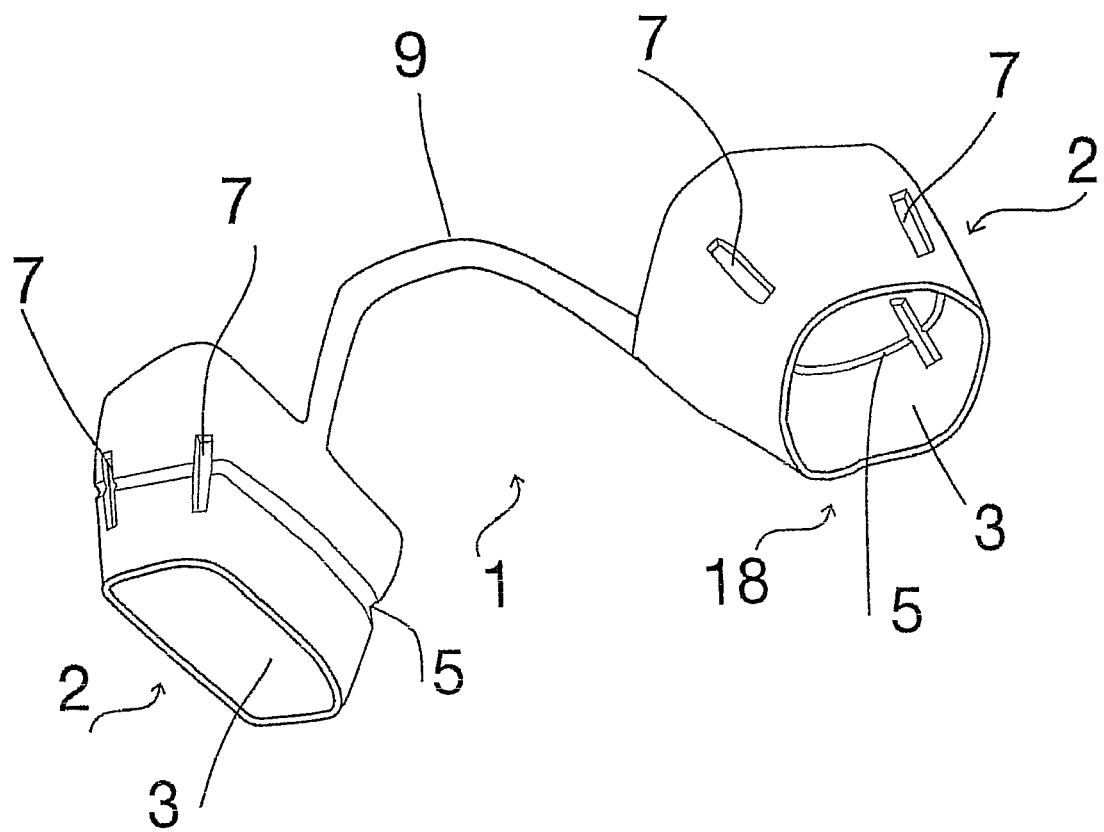
Figur 5

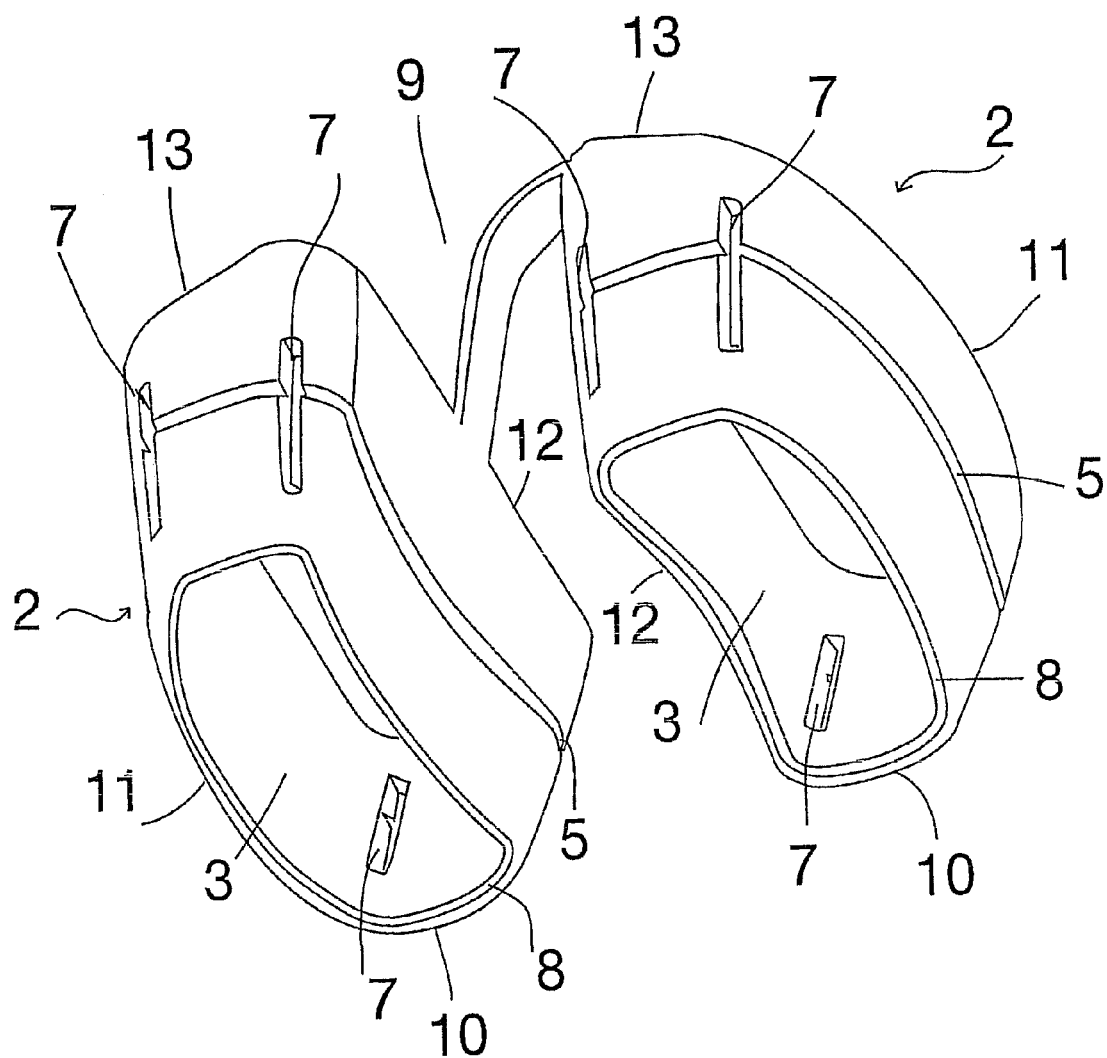
Figur 6

NOSE-DILATING DEVICE

RELATED APPLICATIONS

The present invention claims priority under 35 U.S.C. §120 to international patent application No. PCT/EP2007/011321, filed Dec. 21, 2007, which claims priority under 35 U.S.C. §119 to Swedish Patent Application No. SE 0602802-1, filed Dec. 27, 2006, the disclosures of which are incorporated by reference herein in their entireties.

TECHNICAL FIELD

The present invention relates to an internal nose-dilating device according to the preamble of claim 1.

TECHNICAL BACKGROUND

Breathing through the nose during sleep is highly advantageous compared with breathing through the mouth. When breathing through your mouth the saliva secretion decreases and the mucous membranes become dry. This provides a breeding ground for bacteria and causes dental problems, or an increase thereof, since there is no longer enough fresh saliva for efficacious rinsing. A further aspect of breathing through the mouth is that the teeth are not sufficiently supported and, when the jaws are being separated, thus start to grow at an angle, as there is no resistance.

Breathing through the mouth increases the risk of snoring, since anatomically the throat becomes narrower and the airway smaller as a result of the lower jaw frequently dropping. This constriction of the throat often causes snoring and abnormal breathing. A narrow airway means that you must breathe harder to get enough oxygen, the result being even more snoring sounds.

To reduce or completely eliminate the snorings, snoring guards designed to reposition the lower jaw forward can be used, the guards being positioned in the mouth and retained by an occlusal hold. A drawback of these guards, however, is that they do not bring the jaws tightly together, which means that people with restricted nasal meatuses will tend to open their mouth to breath and, with the mouth open, the effect of snoring guards designed to reposition the lower jaw forward is lost. To improve the situation of these people, the snoring guard designed to reposition the lower jaw forward can be combined with a nose-dilating device, i.e. means arranged outside or inside the nose to dilate the nostrils.

Some people may have a partly deformed nose, which results in an inaccurate air flow and when the person breathes heavily through the nose the nasal walls are simply sucked together, thus obstructing the passage of air. This may also be important, for example, when practicing sports, in which case an optimal air intake is desired.

There are currently a number of methods and means for creating and maintaining a satisfactory passage of air through the nose, for instance by means of external nose-dilating devices, such as nose adhesive strips, or internal nose dilating means, such as plastic springs provided between the nostrils to dilate the nasal openings, and decongestants, such as nose sprays or nose drops.

U.S. Pat. No. 6,004,342 discloses an internal nose-dilating device, which comprises a pair of hollow, cylindrical members, which are made of an elastomeric material and have the shape of a nostril and are designed to be worn inside the nose, a handle portion connecting the two nasal inserts. The drawback of this device is that it cannot be adjusted to different nose shapes or different dilating needs.

WO 8803788 discloses a nose-dilating device in the form of two end portions that are interconnected in a resilient manner, i.e. like a spring-resembling plastic wing, which is inserted into both nostrils, whereby the rigidity of the resilient material causes the front part of the nostrils to dilate. A considerable drawback is here that a large part of the device protrudes from the nose. Due to the strong biasing force, any contact with the device, for instance when touching the pillow or poking it directly, may dislocate the wings, the rigidity of the material thereby causing the plastic wing to fly out of the nose. Accordingly with such a strong biasing force, the product is sensitive to outer influence.

U.S. Pat. No. 5,895,409 discloses an internal nose-dilating device in the form of cylindrical convex tubes, which are inserted into the nose to dilate the nostrils and which are connected by means of a larger external portion. The tubes consist of an open framework having an interior portion and an exterior portion and a plurality of interconnected elongate members, which members extend between the interior and exterior portions and at least one of which is convex. The device described in this document is intended for use in connection with strenuous physical exercise and the administration of anaesthetics. Such devices are often rigid and clearly visible and, above all, rarely adapted to the anatomy of the nose and its different cavities. They are often too long and too bulky and therefore less comfortable and efficacious, since their straight lines make it difficult to keep them positioned in the nose. Furthermore, due to their design they do not fit all types of noses. The air flow obtained when using a completely round insect is not optimal, since a significant part of the air has to pass along the side, its passage being, in fact, partly obstructed by the device. Due to the exterior larger portion there is also an increased risk of the device flying out of the nose when touched.

US 2003150449 discloses a nasal strip, which is attached to the nose by means of adhesive ends for the purpose of nasal dilation. The drawback of devices of this kind is that they are clearly visible and that thorough cleaning of the nose to remove grease is required before attaching them. In many cases, such nasal strips can be used only once, thus generating a significant yearly cost. There is also a risk of the person wearing it being affected by the adhesive. When practicing sports, drops of perspiration form, which may reduce the strength of the strip adhesive. Often, the adhesive used is strong, which implies time-consuming cleaning. Beauty creams cannot be used, which some people consider to be a disadvantage.

There is hence a need for a nose-dilating device which dilates the nostrils to obtain an optimal air intake when sleeping or practicing sports, which device may easily be adjusted to fit all types of nostrils, which due to ethnical origin or injury may be of different shapes, and which is firmly positioned in the nose without being affected when touched. Furthermore, the nasal dilation should be individually adjustable for each nostril. The nose-dilating device should also be discreet and shaped in a suitable manner to fit the anatomy of the nose. It should be positioned inside the nose and expand entirely individually from a centre of its own, which makes each insert independent of the other. Moreover, the nose-dilating device should be easy to clean and adapted for repeated use.

SUMMARY OF THE INVENTION

It is an object of the present disclosure, to provide a nose-dilating device, which eliminates or alleviates at least some of the disadvantages of the prior art.

According to a first aspect, there is provided an internal nose-dilating device comprising two conical inserts, which each have four walls and two openings, a small opening, which during use is oriented inwards towards the nasal cavity and a large opening, which is oriented out from the nose, the inserts being connected by means of a connecting member, which during use is the only part that remains on the outside of the nose, characterised in that the four walls of the inserts are convex at their central portions and provided with a substantially horizontal recess, the recess being arranged along the four walls of the inserts and extending at least partly along the circumference on the outside thereof to form a bulge in the four walls of the inserts, and that the inserts have at least four apertures, and that a reinforced portion is provided along the rounded edge of the small opening, thereby allowing the inserts to be turned inside out.

By "substantially horizontal" is meant that the recess during use of the insert is substantially horizontal or even horizontal.

By way of these features, a bulge in the four walls of the inserts is achieved when the inserts are compressed by applying a light pressure from above and from below, the compression being achieved by the wearer squeezing the insert with his fingers. When inserting the nose-dilating device, the bulge or out-turned fold causes cause an expansion of the nostril walls. After compression, the nose-dilating device retains its expanded shape. Thus, an individually adapted nasal dilation can be obtained by varying the compression of the inserts, which may be important, for instance, if the nose is only partly deformed, in which case a greater expansion is required for one nostril than for the other. During use, the outer convex surface abuts against the inside of the nostril, thereby expanding the nasal passage outwards. Consequently, the insert is designed to lean against the inside of the nostril and the force required to prevent the nasal walls from collapsing is minimal, the inserts having thus a centripetal effect, thereby preventing the nose dilating device from being pushed out of the nostrils.

This configuration optimises nasal dilation and thus the breathing through the nose, with respect to various degrees of nasal dilation and with respect to different nostril shapes.

By the inserts having four apertures and a reinforced portion there is provided a way of allowing the inserts to be turned inside out. When turned inside out, the inserts will have a rounder shape because of the inner tensions in the nose-dilating device, which further improves the nose-dilating effect and also ensures a rounder fit to the nostrils. It is not necessary to turn both inserts inside out; instead one insert at a time can be turned to obtain a greater or smaller dilation of the nostrils. In addition, the reinforced edge along the small opening is rounded so as to be more comfortable for the wearer during insertion and use of the nose-dilating device, by the soft tissue and mucous membranes being protected from chafing.

By the connecting member being the only part of the device which is located outside, the risk of any external influence on the nose-dilating device is minimized.

In one embodiment, the inserts may suitably be kidney-shaped, to better fit the nasal cavity.

In one embodiment, the four openings may, be arranged at the corners of the inserts. The apertures may also be arranged at the long sides of the inserts or, according to one embodiment, at the short sides of the inserts. The arrangement of the apertures will be depending on the shape of the inserts. In one embodiment, the nose-dilating device may be provided with a decongestant.

By "decongestant" is meant a substance such as eucalyptus or menthol, to alleviate the problems associated with nasal congestion in case of a cold or allergies. The decongestant is suitably applied to the inside of the nose-dilating device to avoid direct contact with the mucous membranes.

According to one embodiment the nose-dilating device may be made of an elastic material.

Examples of such material may be, but is not limited to, plastic materials, rubber materials, silicone materials or combinations thereof, the central portion may, for example, be made of a rigid material and the rest of a soft material. Preferably, the material is soft and comfortable for the wearer. The material may also suitably be allergy-tested.

The connecting member may, according to one embodiment, be rigid and substantially U-shaped.

By the rigid and substantially U-shaped connecting member there is provided means for ensuring that the inserts are not inserted too far in the nostrils and to centre the inserts in the nose. The rigidity of the connecting member may also aid in the adjustment of the nose-dilating device once it has been inserted into the nose of the wearer.

According to a second aspect of the present disclosure there is provided a method for changing the size of a nose-dilating device, according to the first aspect, which comprise compressing the inserts, by applying an axial force, by the wearer squeezing the insert with his fingers.

By "axial force" is meant that the wearer squeezes the insert at both the small and large opening and thereby compresses the inserts.

By this method there is provided an easy way of changing the size of the inserts. The compression will contribute to the bulging of the walls of the inserts, and hence to a different size of the insert.

According to a third aspect there is provided method for using a nose-dilating device, according to the second aspect, and inserting the inserts into the nostrils of the wearer. According to a fourth aspect there is provided a method for changing the size of a nose-dilating device, according to the first aspect, comprising turning at least one insert inside out.

By turning at least one insert inside out a more rounded shape of the insert is achieved, which may fit more properly in a nostril with a more rounded shape.

According to a fifth aspect there is provide a method for using a nose-dilating device, according to the fourth aspect, and inserting the inserts into the nose of the wearer.

By the changing of the size prior to the insertion into the nose a more proper fit in the nostril may be provided.

The methods, according to the third and fifth aspect, may further comprise centring the inserts in the nose by adjusting the angle which the device has in the nose.

The insert may be centred by moving the connecting member.

By adjusting the position of the inserts, when they have been inserted into the nostrils of the wearer, there is provided a way obtaining an optimal angle of the nose-dilating device when positioned in the nose. According to a sixth aspect of the present solution there is provided a method for changing the size of a nose-dilating device, which comprise heating up the device, to a temperature where the material softens, and compressing the inserts, by applying an axial force, by the wearer squeezing the insert with his fingers.

By "axial force" is meant that the wearer squeezes the insert at both the small and large opening, thereby compressing it.

According to a seventh aspect of the present solution there is provided a method for using a nose-dilating device, according to the sixth aspect, and inserting the inserts into the nostrils of the wearer.

According to an eight aspect there is provided a method for changing the size of a nose-dilating device, which comprise heating up the device, to a temperature where the material softens, and turning at least one insert inside out.

According to a ninth aspect there is provided method for using a nose-dilating device, according to the eight aspect, and inserting the inserts into the nostrils of the wearer.

By heating up the device before compressing the inserts and/or turning the inserts inside out there may be provided an even better way of adjusting the size of the inserts, since the material has been made softer and hence more pliable by the heating.

By the changing of the size before insertion into the nose a more proper fit in the nostril may be provided.

The methods according to the seventh and ninth aspects, further comprising centring the inserts in the nose by adjusting the angle which the device has in the nose. The insert may be centred by moving the connecting member. By adjusting the position of the inserts, when they have been inserted into the nostrils of the wearer, there is provided a way obtaining an optimal angle of the nose-dilating device when positioned in the nose.

DESCRIPTION OF THE DRAWINGS

Embodiments of the present solution will now be described, by way of example, with reference to the accompanying schematic drawings.

FIG. 1 is a schematic cross sectional view of a nose-dilating device.

FIG. 2 is a schematic perspective view over the small openings.

FIG. 3 is a schematic perspective view over the large openings.

FIG. 4 is a schematic cross sectional view of both inserts turned inside out.

FIG. 5 is a schematic perspective view of a nose-dilating device with one insert turned inside out.

FIG. 6 is a schematic perspective view of one embodiment of the present solution.

DESCRIPTION OF EMBODIMENTS

FIGS. 1-5 illustrates a nose-dilating device 1 comprising two inserts 2, which have recesses 6 through which air flows when the inserts 2 are positioned in the nose. FIGS. 2 and 3 illustrate that the insert 2 has two short sides 10, 13 and two long sides 11, 12 and two openings: a small opening 3, which during use of the nose-dilating device is oriented towards the inner cavity of the wearer's nose, and a large opening 4, which during use is oriented out of the nose.

FIGS. 2 and 3 illustrates that the openings 3 and 4 may be substantially oval-shaped to fit the shape of the nostril.

FIG. 1 illustrate that the insert 2, may substantially be conical.

FIG. 1 illustrate that the walls 10, 11, 12, 13 of the insert are convex at their central portion with a convex surface 16 on the outside of the inserts and a concave surface 17 on the inside thereof.

FIG. 1 illustrate that the inserts 2 are interconnected by means of a connecting member 9. The connecting member may, according to one embodiment be substantially in the form of a U-shaped strip. The connecting member 9 may also consist of two parts, one of which is attached to the long side 12 adjacent the large opening 4.

The inserts 2 and the connecting member 9 may suitably be formed in one piece. The rigidity and U-shape of the connecting member 9 are also intended to facilitate adjustment of the nose-dilating device 1 when inserting it in the nose, in order to obtain an optimal angle of the nose-dilating device 1 when positioned in the nose.

FIGS. 2 and 3 illustrates that the short sides 10 and 13 may be beveled, which makes the long side 12 longer, in a longitudinal direction, than the long side 11.

The inserts 2 are provided with a recess 5 (FIGS. 1-6), which recess 5 is arranged along the four walls 10, 11, 12, 13 of the inserts 2 and extends at least partly along the circumference on the outside 16 thereof. The recess may, according to one embodiment, substantially be elongate. The recess 5 may, according to one alternative, substantially be a groove. The recess 5 may, according to one embodiment, be designed as a single continuous recess. The recess 5 may, according to an alternative embodiment, be intermittently slotted. Preferably, the recess 5 is arranged on the outside 16 of the insert 2 to achieve a directional, thin breaking point, the result of which is that when a pressure is applied to the nose dilating device 1, the central portion of the sides 10, 11, 12, 13 bulges even more, which may cause a greater expansion of the nostrils as the device is being inserted in the nose. By compressing the respective inserts 2 to a varying degree, an individual width may be obtained and, thus, an individual expansion of each nostril.

FIGS. 1-3 illustrates that the inserts 2 are provided with at least four apertures 7, which according to one embodiment may be arranged at the corners 15. The apertures 7 may, according to another embodiment, be arranged on the long sides 11, 12. The apertures 7 may even, according to a further embodiment, be arranged on the short sides 10, 13. The position of the apertures will be depending on the design of the nose-dilating device.

According to one embodiment, said apertures 7 may be oriented away from the large opening 4 in the direction of the small opening 3.

The small opening 3 has a rounded edge, which is also reinforced 8 (FIG. 1).

FIG. 4 illustrates that turning the insert/inserts 2 inside out may provide them with a rounded shape 18, said shape enabling a greater expansion of the nose and, thus, ensuring that the insert 2 fits, for example, in nostrils with a rounded shape or significantly deformed nostrils.

FIG. 5 illustrates the normal shape of the inserts 2 compared to an insert, which has been turned inside out. FIG. 5 also illustrates that, optionally, only one of the inserts 2 may be turned.

FIG. 6 illustrates that, the inserts 2 may, in one embodiment, be kidney-shaped. The inserts 2 may according to alternative embodiments also be shaped in other suitable ways (not shown).

The inserts may be formed by an elastic material. The material may, according to alternative embodiments, be plastic materials, rubber materials, silicone materials or combinations thereof.

The device 1 may comprise different stiffness in different parts of the device. The central portion of the insert may, according to one embodiment, be made of a rigid material and the rest of the insert of a soft material.

The inserts 2 may, according to an alternative embodiment, be reinforced on the inside to increase stability and reduce air resistance.

Preferably, the material is transparent or flesh-coloured to ensure that the inserts are discrete during use.

The device 1 may, according to one embodiment, be heated before the inserts 2 are compressed or before at least one of the inserts is turned inside out. The heating may be achieved by means of holding the device in hot water for a period of time. The water may, according to one embodiment, be heated to from about 45° C. to about 50° C. and the period of time may range from about 20 seconds to about 40 seconds. The device may alternatively be heated by the wearer holding the device in, e.g. his or hers hand.

It will be appreciated that a number of modifications of the embodiments described above are possible within the scope of the invention, as defined by the appended claims. For instance, the inserts 2 and the connecting member 9 of the invention could be provided in the form of a net (not shown) to reduce any injury due to chafing against tissue and mucous membranes and to make the inserts 2 and connecting member 9 more resilient.

What is claimed is:

1. An internal nose-dilating device, comprising two conical inserts, which each have four walls and two openings:
    a small opening, which during use is oriented inwards towards the nasal cavity, and a large opening, which is oriented out from the nose, the inserts being connected by means of a connecting member, which during use is the only part that remains on the outside of the nose, characterized in that the four walls of the inserts are convex at their central portions and provided with a substantially horizontal recess, the recess being arranged along the four walls of the inserts and extending at least partly along the circumference on the outside thereof to form a bulge in the four walls of the inserts;
    that the inserts have at least four apertures, the at least four apertures disposed substantially perpendicular to the horizontal recess; and
    that a reinforced portion is provided along a rounded edge of the small opening, thereby allowing the inserts to be turned inside out.

2. A nose-dilating device as claimed in claim 1, wherein the inserts are kidney-shaped.

3. A nose-dilating device as claimed in claim 1, wherein the four apertures are arranged at the corners of the inserts.

4. A nose dilating device as claimed in claim 1, wherein the four apertures are arranged at the long sides of the inserts.

5. A nose dilating device as claimed in claim 1, wherein the four apertures are arranged at the short sides of the inserts.

6. A nose dilating device as claimed in claim 1, wherein the nose-dilating device is provided with a decongestant.

7. A nose-dilating device as claimed in claim 1, wherein the nose-dilating device is made of an elastic material.

8. A nose-dilating device as claimed in claim 1, wherein the connecting member is rigid and substantially U-shaped.

9. A method for changing the size of a nose-dilating device, as claimed in claim 1, comprising:
    compressing the inserts, by applying an axial force, by the wearer squeezing the inserts with his fingers.

10. A method for using a nose-dilating device as claimed in claim 9, further comprising:
    inserting the inserts into the nostrils of the wearer.

11. The method as claimed in claim 10, further comprising:
    centring the insert in the nose by adjusting the angle which the device has in the nose.

12. The method as claimed in claim 11, wherein the insert is centred by moving the connecting member.

13. A method for changing the size of a nose-dilating device as claimed in claim 1, comprising:
    turning at least one insert inside out.

14. A method for using a nose-dilating device as claimed in claim 13, further comprising:
    inserting the inserts into the nose of the wearer.

15. A method for changing the size of a nose-dilating device as claimed in claim 1, comprising:
    heating up the device, to a temperature where the material softens; and
    compressing the inserts, by applying an axial force, by the wearer squeezing the inserts with his fingers.

16. A method for using a nose-dilating device as claimed in claim 15, further comprising: inserting the inserts into the nostrils of the wearer.

17. The method as claimed in claim 16, further comprising:
    centring the insert in the nose by adjusting the angle which the device has in the nose.

18. The method as claimed in claim 17, wherein the insert is centred by moving the connecting member.

19. A method for changing the size of a nose-dilating device as claimed in claim 1, comprising:
    heating up the device, to a temperature where the material softens; and
    turning at least one insert inside out.

20. A method for using a nose-dilating device as claimed in claim 19, further comprising:
    inserting the inserts into the nostrils of the wearer.

* * * * *